United States Patent
Shapiro

[11] Patent Number: 5,324,295
[45] Date of Patent: Jun. 28, 1994

[54] DRILL GUIDE FOR SURGICAL PINS

[76] Inventor: Michael R. Shapiro, 24818 Alexandra Ct., Calabasas, Calif. 91302

[21] Appl. No.: 873,326

[22] Filed: Apr. 24, 1992

[51] Int. Cl.$^5$ .............................. A61F 5/00; A61F 2/32
[52] U.S. Cl. .......................................... 606/86; 606/96
[58] Field of Search ............... 606/96, 97, 98, 86, 606/87, 88, 89, 90, 79, 104, 105

[56] References Cited

U.S. PATENT DOCUMENTS

| | | | |
|---|---|---|---|
| 2,181,746 | 11/1939 | Siebrandt | 606/96 |
| 2,301,500 | 11/1942 | Anderson | 606/96 |
| 2,531,734 | 11/1950 | Hopkins | 606/97 |
| 2,697,433 | 12/1954 | Zehnder | 606/96 |
| 3,704,707 | 12/1972 | Halloran | 606/97 |
| 4,037,592 | 7/1977 | Kronner | 606/97 |
| 4,235,428 | 11/1980 | Davis | 606/96 |
| 4,335,715 | 6/1982 | Kirkley | 606/87 |
| 4,421,112 | 12/1983 | Mains | 606/96 |
| 4,952,213 | 8/1990 | Bowman | 606/79 |
| 5,078,719 | 1/1992 | Schreiber | 606/96 |

*Primary Examiner*—Michael A. Brown
*Attorney, Agent, or Firm*—Robbins, Berliner & Carson

[57] ABSTRACT

A convergence guide is provided that is particularly useful in arthroscopic knee surgery to allow the drilling of two guide pins starting at different places on the outside of the knee but converging to the same spot in the center of the knee. A pair of offset members are arranged in the convergence guide to facilitate adjustment of the position of the pins to converge at one of a plurality of predetermined distances. Each offset member is itself useful as an offset guide to drill a second guide pin through a bone in parallel proximity to a first pin disposed in the bone. The guide has a plurality of parallel offset holes set at predetermined distances in an array for enabling the guide to slide over and pivot around the first pin through one hole and receive the second pin through another hole.

16 Claims, 3 Drawing Sheets

DRILL GUIDE FOR SURGICAL PINS

FIELD OF THE INVENTION

The present invention relates generally to drill guides for surgical guide pins such as are used in arthroscopic surgery.

BACKGROUND AND SUMMARY OF THE INVENTION

The present invention is useful in a variety of surgical procedures but is particularly useful in arthroscopic surgery of the knee and most particularly in facilitating the surgical repair or reconstruction of the anterior cruciate ligament (ACL). Sports injuries to the knee often result in tearing of the ACL. If the injured person is a professional athlete, it may be critical to full recovery and to his or her ability to further compete professionally to repair or reconstruct the ligament so that is mimics as much a possible the function of the original ACL.

The anatomically correct procedure would be to make a double band graft where the graft is divided into the two major bands of the ACL, i.e., the anterior medial band and the posterior lateral band, securing each band to the femur. However, it is very difficult to design an operation to provide such an arrangement. Most surgical graft procedures have utilized a single graft joined at one center point on the tibia and at one center point on the femur using bone-tendon-bone blocks taken from the patient's patella and fixed by an interference fit in drilled bone tunnels. In concept, center-to-center attachment of a single band of reasonable size is supposedly "isometric" so that the fiber does not change over its length in any position of knee flexion or extension. However, in fact, not all portions of the graft are going to be perfectly isometric, so that if the points of attachment turn out to be wrong, there is a tendency for the graft to stretch, making the knee looser than it would ordinarily be. Moreover, if the tibial attachment is too far forward, the graft can impinge against the roof of the intercondylar notch as the knee is extended, preventing the knee from straightening out. When that happens, a notchplasty may be required or the graft moved further backwards, entailing additional surgery.

In another procedure used with certain ACL tears, up to 20 sutures are placed in each of the stumps of the torn ligament. Using a drill guide, a guide pin is inserted in back of the knee and then an arthroscopic port is formed using a cannulated drill over the pin. Half of the sutures are drawn through the port, the other half through the center of the knee and around the back of the knee where they are tied to the first half. Several problems arise with such a procedure. First, the procedure requires additional dissection around the back of the knee to retrieve the sutures. Second, the sutures are drawn over tendon structure making it difficult to tie the sutures. Third, placement of the reattachment is less anatomic when you have to draw the sutures over the back of the knee than if you took them all through an anatomic attachment site.

The present invention solves the foregoing problems associated with reconstruction of the ACL as well as those associated with suture repair of the ACL. In one embodiment a convergence guide is provided in which converging guide holes allow the drilling of two pins starting at different places on the outside of the knee but converging to the same spot in the center of the knee. For example, the pins can be drilled to converge from the lateral area of the knee where a surgeon would normally be drilling a hole through the femoral condyle to retrieve sutures. The sutures could then be brought out through the separate holes on the lateral side providing a bone bridge over which the sutures could be tied.

Use of the convergence guide also facilitates a double banded graft such as used in semi-tendonosis anatomic reconstruction (known by the acronym STAR) and is also applicable to dacron grafts as well as to achilles tendon or patellar tendon cadaver grafts, all of which are well known grafts but which are difficult to perform or have the problems referred to above. The STAR procedure is based on the observation that the anterior medial band ducks under the roof of the intercondylar notch at a flatter angle than does the posterior lateral band. The anterior medial band starts further forward on the tibia but then goes at a relatively flat angle to a point further back. The posterior lateral band starts at a point further back on the tibia and goes at a relatively steep angle to a point further forward. As a result, fibers of the posterior lateral band are tighter in extension of the knee whereas fibers of the anterior medial band are tighter at 45 degrees of knee flexion. Using the convergence guide allows the two anatomic bands to be placed in such a way that the posterior lateral band can be tightened in extension and the anterior medial band can be tightened at 45 degrees of knee flexion thereby mimicking the natural disposition of these bands. The bands can then be sutured to one another and/or stapled down over the bone bridge formed by the separation of the converged holes on the lateral side of the knee.

Since different patients will require the convergence point to be located at different distances from the guide, a plurality of converging guide holes are provided. This is accomplished by means of a pair of cylindrical offset members slidably carried in respective converging cylindrical bores on the convergence guide. One offset member is used to slide over and pivot around a first guide pin that has been drilled into the bone. The other offset member is used as a guide to receive a second guide pin to be drilled so as to converge with the first pin. Each offset member contains along its length a plurality of parallel holes offset predetermined distances from each other, enabling the surgeon to choose any of a plurality of convergence distances.

In a particular embodiment, the holes in each offset member are disposed in a rectangular array of at least nine holes including a central hole, corner holes and side holes. The center-to-center distance between each of two opposite side holes and the central hole is 2 mm and the center-to-center distance between each corner hole and the central hole is 3 mm. As a result, parallel offsets of exactly 2, 3, 4 and 6 mm are available to the surgeon along with the intermediate distance of about 4.5 mm. This results in convergence distances into the bone in the range of about 30 to about 40 mm. In still another embodiment, the proximal side of the convergence guide is concave to better fit a patients knee.

By providing converging holes in slidably disposed members, the convergence guide is readily disassembled. Slots are defined entirely through the sidewall of the convergence guide to and coextensive with respective cylindrical bores, each slot being wider than the thickness of the guide pin. The convergence guide is removed while leaving the converging pins in place by sliding the offset members out of their bores and then withdrawing the convergence guide while the pins pass through the slots.

Other problems that arise in the course of arthroscopic surgery relate to difficulties in properly placing or aligning guide pins. The surgeon attempts to locate the pins so that they converge at the inner surface of the knee, but initial placement will generally require some guessing and a poor estimate of the convergence point may require redrilling the pin. Even a single pin can be badly placed or be misaligned due to the tendency of the drill to wander while drilling. Taking the pin out and redrilling is difficult because of the tendency of the pin forming the new hole to slide into the old hole during drilling.

Prior mechanical approaches to this problem are not quite satisfactory. One device, known as an Acufex, has a lug formed with a nubbin on one side that is placed in the bad hole after the pin is removed. The lug has a guide hole offset from the center of the nubbin by 3 mm which can pivot around in any direction to drill a parallel hole 3 mm from the old hole. One problem is that it is often difficult to find the small hole left when the pin is removed. Another problem is that the surgeon has only the option of moving the pin the single fixed distance of 3 mm from the original hole, which limits the surgeon's choices.

Another device is known as the Lemoire offset and has three parallel holes in a triangular array, each hole being 3 mm center-to-center from each other. The offset is slid onto the bad pin and then pivoted around the pin to a desired location, but limited to 3 mm from the original hole where a new pin is drilled parallel to the first pin. As with the Acufex, the surgeon has only the limited option of moving the pin the single fixed distance of 3 mm from the original hole.

These problems are alleviated by another embodiment of this invention in which one of the cylindrical offset members is used as a unique offset guide to enable a second pin to be drilled through a bone in close parallel proximity to a first pin disposed in the bone. The cylindrical offset member is fitted with a clamp handle and is used by sliding the offset member over the badly placed pin through one of the parallel holes and then pivoting it in a desired direction. A new pin is then placed at a desired offset distance and drilled into the bone in parallel proximity to the first pin without the danger of sliding into the first hole which is still occupied by the first pin. After successfully inserting the second pin into the bone, the first pin can be removed. The unique array of parallel holes allows great flexibility to the surgeon in correcting poor pin placement.

DETAILED DESCRIPTION OF THE PREFERRED EMBODIMENTS

Figure 1:
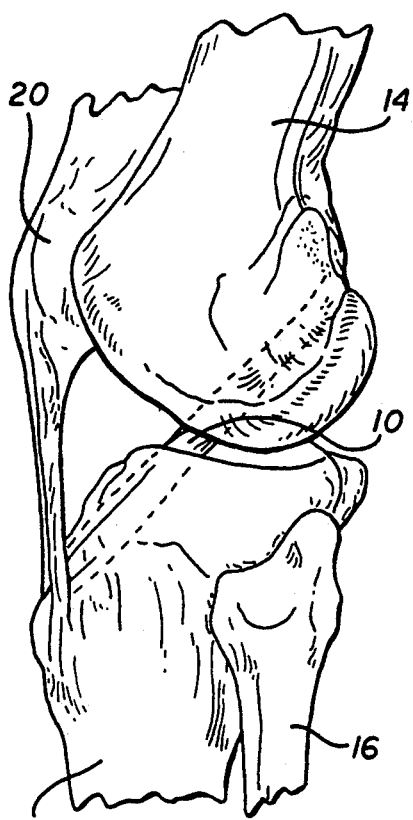
FIG. 1 is view of the lateral side of the bone structure of a left knee.
Figure 2:
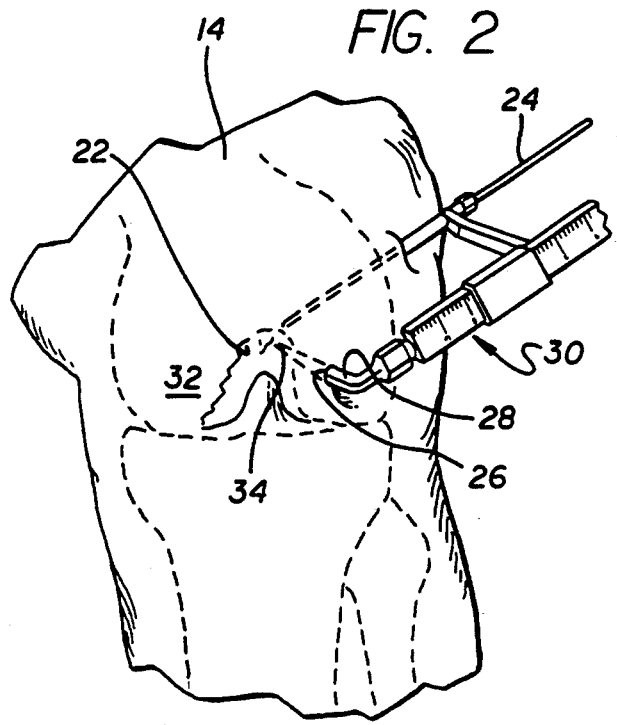
FIG. 2 is a front (anterior posterior) view of the knee showing the placement of a guide pin in the femur using a prior art drill guide.

The construction and use of the convergence guide of the present invention will be described in conjunction with the insertion of standard guide pins through the bone structure of a knee. A standard cannulated drill is placed over an inserted guide pin to drill an arthroscopic port or hole. Part of the bone and tendon structure of a typical knee is illustrated in FIG. 1 including the ACL 10 joining the tibia 12 and femur 14. Also shown is the fibula 16, femoral condyle 18 and patella or knee cap 20. The intercondylar notch 22 is shown in FIG. 2 which also illustrates a standard technique of placing a guide pin 24 through the femur 14. An inferiormedial arthroscopic port 26 is reamed through the femur 14 adjacent the intercondylar notch 22 using standard arthroscopic techniques. The guide locator portion 28 of a standard, adjustable ruled drill guide 30 (before assembly of the drill guide) is passed through the inferiormedial port while being observed through another arthroscopy port or hole at 32 (not shown). The tip 34 of the locator portion 28 is positioned just anteriormedial to the central portion of the tibial ACL attachment. The rest of the drill guide 30 is then assembled and oriented toward the anteriormedial portion of the tibia. The position of the locator portion is checked arthroscopically and the guide pin 24 (e.g., 2.37 mm diameter) is inserted through the drill guide 30, skin, and anterior portion of the tibia, just through the cortex of the intercondylar eminence. The drill guide is disassembled and removed, leaving the guide pin 24 in place.

Figure 3:
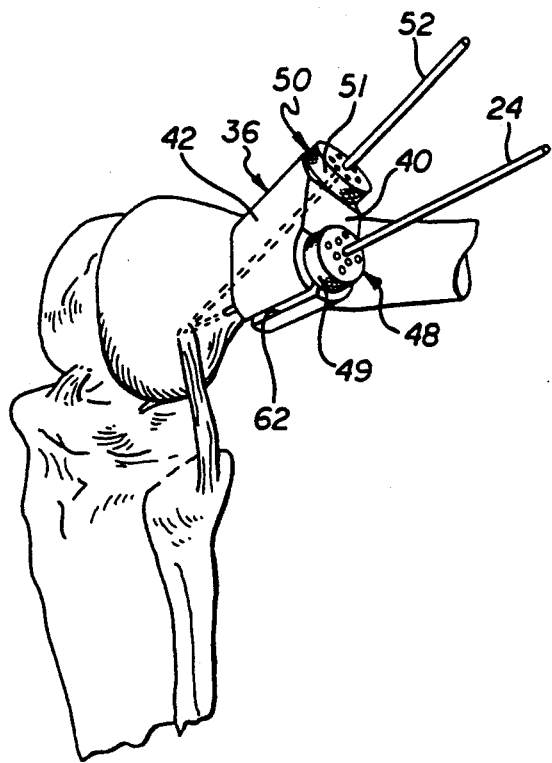
FIG. 3 is a lateral view of part of the bone structure of a flexed knee showing the convergence guide of this invention in place with a pair of converging guide pins.
Figure 4:
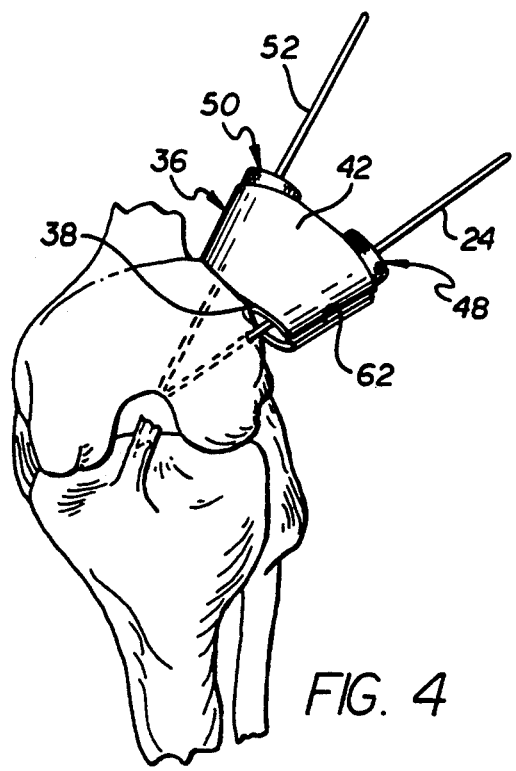
FIG. 4 is a front view of part of the bone structure of the knee showing the convergence guide and converging guide pins.
Figure 7:
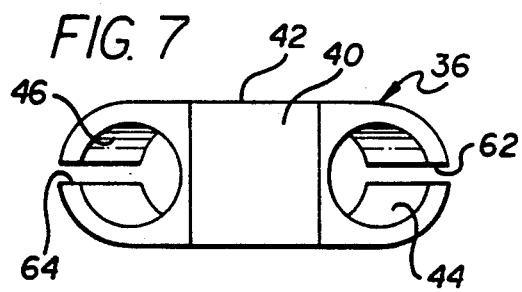
FIG. 7 is a top plan view of the convergence guide without the offset members.
Figure 8:
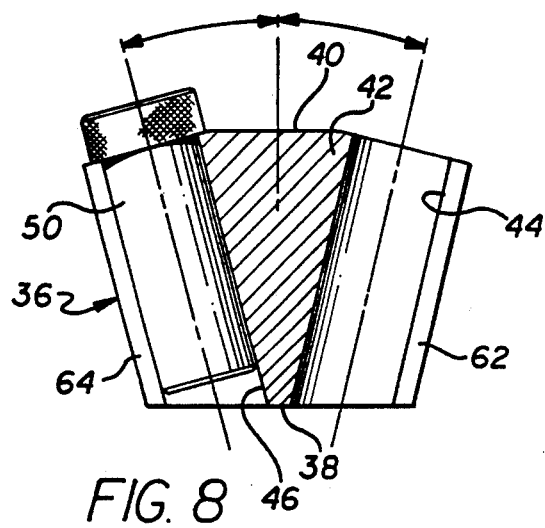
FIG. 8 is a cross sectional view of the convergence guide of FIG. 7 showing the cylindrical bores, and also showing an elevational view of one of the offset members disposed in a bore.

Referring to FIG. 3, through an incision in the skin, a convergence guide 36 of this invention is slid over the guide pin 24. The convergence guide 36 has a proximal side 38 (FIG. 4) placed against the entry surface of the bone, an opposite distal side 40, and a sidewall 42 between the proximal and distal sides. Referring additionally to FIGS. 7 and 8, the convergence guide 36 defines a pair of cylindrical bores 44 and 46 from the distal side 40 to the proximal side 38 formed to respectively slidably receive offset members 48 and 50.

Figure 9:
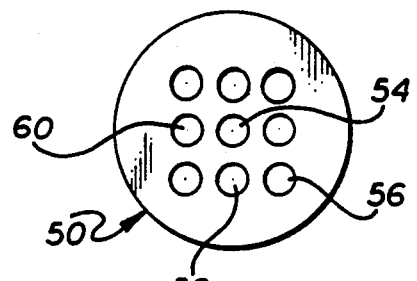
FIG. 9 is a top plan view of one of the offset members.

Although the offset members 48 and 50 are identical, one of the offset members 48 serves as an offset pivot to slide over and pivot around the inserted guide pin 24. The other offset member 50 serves as an offset guide to receive another guide pin 52. Referring additionally to FIG. 9, the hole array of the offset guide member 50 is shown, but the array is identical for the offset pivot member 48. Each offset member contains a plurality of parallel holes arranged in an array, in this embodiment, a rectangular array of at least nine holes including a central hole 54, corner holes 56 and side holes 58 and 60. The center-to-center distance between each of two opposite side holes 58 and the central hole 54 is 2 mm and the center-to-center distance between each corner hole 56 and the central hole 54 is 3 mm (the center-to-center distance between the other side holes 60 and the central hole 54 is 2.23. As a result, parallel offsets of exactly 2, 3, 4 and 6 mm are available to the surgeon along with the intermediate distance of about 4.5 mm (between a corner hole 56 and a side hole 58).

The offset members have flange tops 49 (FIG. 5) and 51, respectively to limit the extent of sliding in the bores 44 and 46. The bores 44 and 46 are spaced from each other a first predetermined distance on the distal side 40 and a shorter predetermined distance on the proximal side 38 so that any one of the offset guide holes converges with any one of the offset pivot holes at a point spaced at one of a plurality of predetermined distances from the proximal side 38 of the convergence guide 36. This results in convergence distances into the bone (i.e., from the proximal side 38 of the convergence guide 36) in the range of about 30 to about 40 mm (35 mm when the guide pins 24 and 52 are located in the respective central holes 54). By inserting the pin 52 into an appropriate hole in the offset guide member 50, the pin 52 can be drilled to converge with the first pin 24 at a desired location in the intercondylar notch 34.

An advantageous feature of this invention is the ability of the surgeon to easily correct poorly placed pins. After the guide pin 52 is drilled into the bone, whether it has properly converged with the first pin 24 can be observed through the arthroscopic port 32. If it is found that the convergence point is wrong, then a new convergence hole can be drilled by leaving the correctly placed pin in the bone and withdrawing the poorly placed pin. The convergence guide can either be pivoted to a shifted location or the pin 52 can be relocated to another hole between 2 and 6 mm offset from the original hole. The parallel offset holes assure placement without the danger of having the relocated pin slide into the previous hole.

Figure 5:
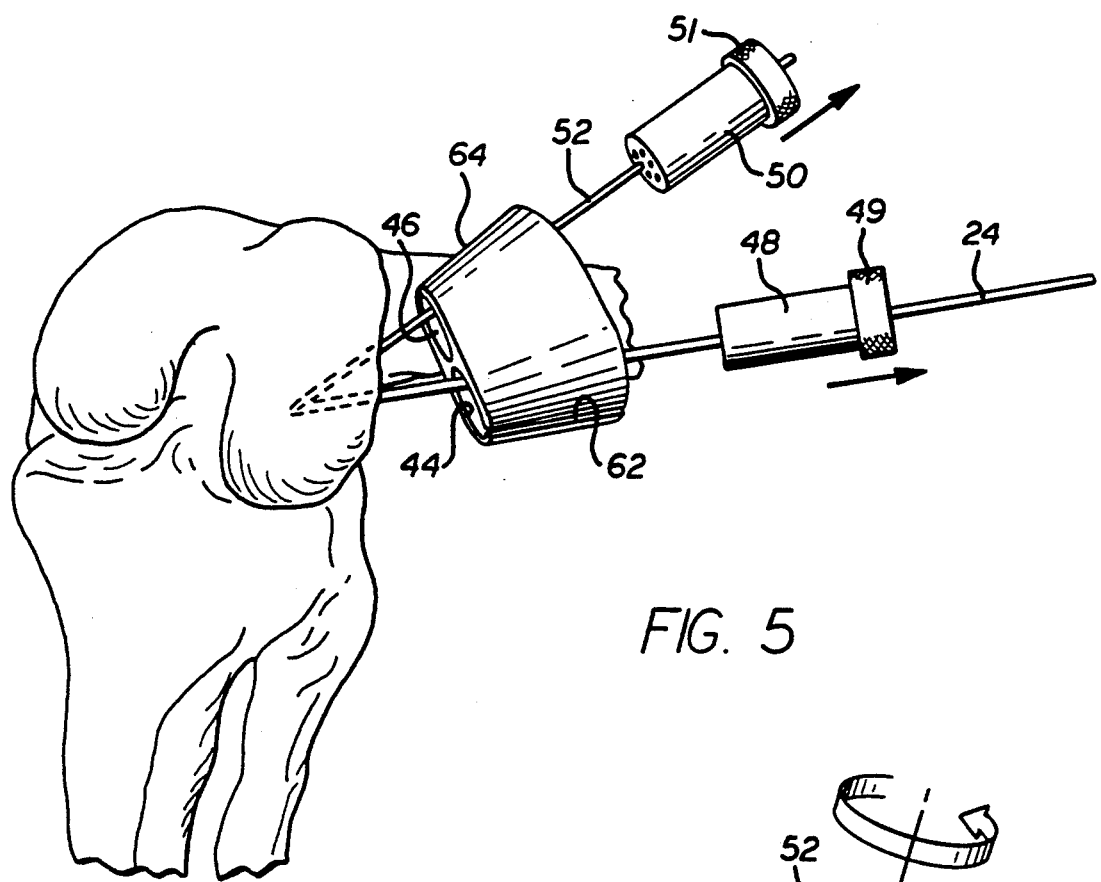
FIG. 5 is a view showing disassembly of the convergence guide by sliding the offset members out of their bores in the convergence guide.
Figure 6:
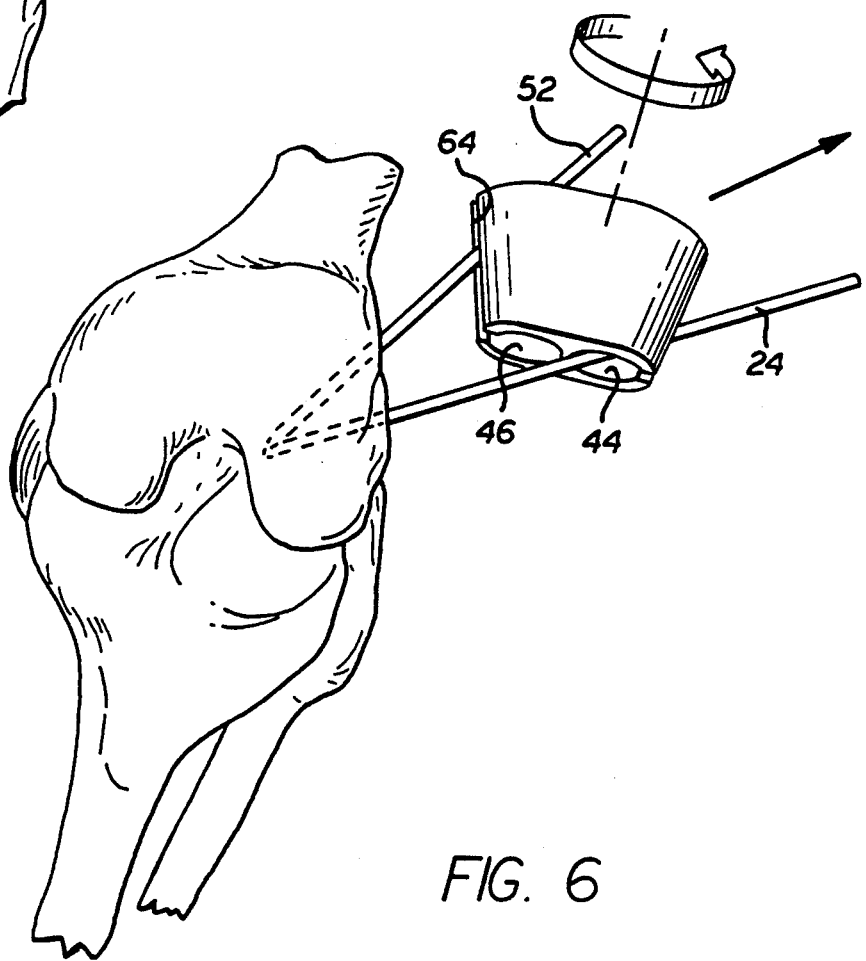
FIG. 6 is a view showing removal of the convergence guide while the guide pins pass through slots in the convergence guide, leaving the guide pins in the bone.

Referring to FIGS. 3, 4, 7 and 8, the convergence guide 36 defines a pair of slots 62 and 64, each wider than the expected thickness of the guide pin, formed entirely through the sidewall 42 to and coextensive with respective bores 44 and 46. When the offset members 48 and 50 are in the bores 44 and 46, the slots 62 and 64 are closed. Referring to FIGS. 5 and 6, to remove the convergence guide from the implanted pins 24 and 52, the offset members 48 and 50 are slid out of the bores 44 and 46 over the respective pins 24 and 52. The convergence guide 36 is then withdrawn, the pins 24 and 52 passing through slots 62 and 64, while the pins 24 and 52 remain securely in the bone, all as shown by the arrows in FIGS. 5 and 6.

Figure 10:
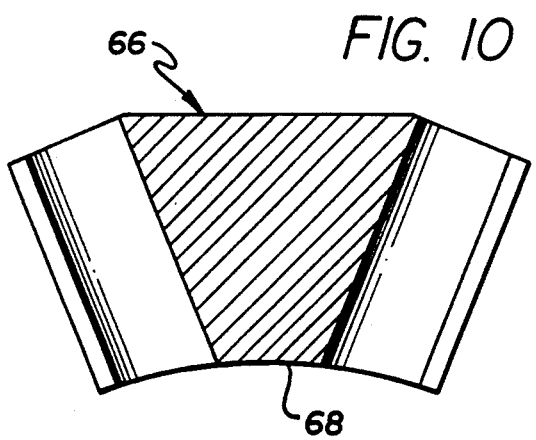
FIG. 10 is a cross sectional view of a convergence guide of another embodiment showing the cylindrical bores and having a concave proximal side.

Referring to FIG. 10, in another embodiment a convergence guide 66 is provided in which the proximal side 68 is concave to permit a closer fit to the femoral bone. Other modifications could be made. For example, the proximal side could have a more femoral configuration, or a handle could be provided extending from the sidewall, normal to the offset holes.

Figure 11:
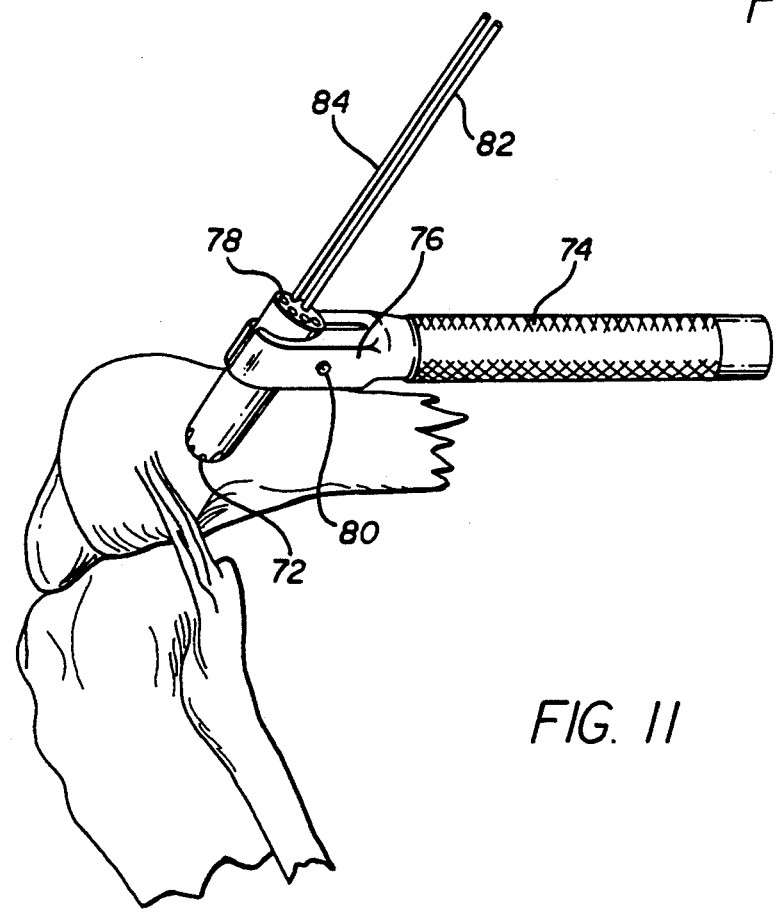
FIG. 11 is view of the bone structure of a knee, similar to that in FIG. 3, showing the use of one of the offset members as an offset guide.

Referring to FIG. 11, still another embodiment is shown in which an offset member is used as an offset guide 70 for correcting a badly placed pin insertion. While an offset member identical to the convergence guide offset member 48 or 50 could be used, the offset guide 70 in this embodiment is formed without the flange 49 or 51. Moreover, in this embodiment the offset guide 70 has a convex bottom 72. In all other respects, the offset guide 70 is formed identical to the offset member 48 or 50. In addition, the offset guide is provided with a handle 74 that includes an integral clamp member 76 to secure the handle to the offset member 70 normal to its holes 78. The handle clamp 76 is tightened about the offset member by means of a set screw 80.

In use, the offset guide 70 is slid over to pivot around a badly placed guide pin 82 through one of the holes 78. A substitute guide pin 84 is inserted in another hole 78 in parallel proximity to the first pin 82. Once the substitute pin 84 is in place, the first pin can be withdrawn.

I claim:

1. A device to guide the drilling of a second pin through an entry surface of a bone so as to substantially converge at an opposite surface of the bone with a first pin disposed in said bone, comprising:

a convergence guide having a proximal side to be placed adjacent the surface of said bone, and an opposite distal side;

an offset guide member containing a plurality of parallel offset guide holes at predetermined distances from each other including at least one guide hole for receiving said second pin, said convergence guide defining means for slidably receiving and disposing said offset guide member and defining at least one pivot hole for enabling said guide to slide over and pivot around said first pin, said holes extending from said distal side to said proximal side, said guide holes spaced from said pivot hole predetermined distances on said distal side and respective shorter predetermined distances on said proximal side whereby any one of said guide holes converges with said pivot hole at one of a plurality of predetermined distances from the proximal side of said convergence guide; and means for releasing said convergence guide from said pins while said pins remain in said bone.

2. The device of claim 1 in which said plurality of offset guide holes are disposed in a rectangular array of at least nine holes.

3. The device of claim 2 in which said pivot hole is one of a plurality of parallel offset pivot holes defined by said convergence guide in a rectangular array of at least nine holes at predetermined distances from each other.

4. The device of claim 1 in which said pivot hole is one of a plurality of parallel offset pivot holes defined by said convergence guide at predetermined distances from each other.

5. The device of claim 1 in which said convergence guide includes a sidewall between said proximal and distal sides, said means for slidably receiving said offset guide member comprises a channel formed through said convergence guide from said distal side to said proximal side, and said releasing means comprises a slot wider than the expected thickness of said second pin, formed entirely through said sidewall to and coextensive with said channel whereby to enable release of said convergence guide from said pins by sliding said offset guide member out of said channel and then withdrawing said convergence guide while said second pin passes through said slot.

6. A device to guide the drilling of a second pin through an entry surface of a bone so as to substantially converge at an opposite surface of the bone with a first pin disposed in said bone, comprising:

an offset guide member containing a plurality of parallel offset guide holes at predetermined distances from each other, each guide hold being formed to receive said pin;

an offset pivot member containing a plurality of parallel offset pivot holes at predetermined distances from each other, each pivot hole being formed to receive and pivot around said first pin;

a convergence guide having a proximal side to be placed adjacent the entry surface of said bone, and an opposite distal side, said convergence guide defining means for slidably receiving and convergingly disposed said offset guide member and said offset pivot member whereby said holes extend from said distal side to said proximal side, said guide holes spaced from said pivot holes first predetermined distances on said distal side and respective shorter predetermined distances on said proximal side so that said plurality of parallel guide holes converge with said plurality of parallel pivot holes at points spaced at different predetermined distances from the proximal side of said convergence guide; and means for releasing said convergence guide from said pins while said pins remain in said bone.

7. The device of claim 6 in which said convergence guide includes a sidewall between said proximal and distal sides, said means for slidably receiving said offset guide member and said offset pivot member comprises respective channels formed through said convergence guide from said distal side to said proximal side, and said releasing means comprises a pair of slots, each wider than the expected thickness of the pins thereat, formed entirely through said sidewall to and coextensive with respective channels whereby to enable release of said convergence guide from said pins by sliding said offset guide member and said offset pivot member out of their respective channels and then withdrawing said convergence guide while said pins pass through said slots.

8. The device of claim 7 in which said offset guide member and said offset pivot member are each cylindrical members and said channels are cylindrical bores convergingly formed through said convergence guide.

9. A device to guide the drilling of a second pin through an entry surface of a bone so as to substantially converge at an opposite surface of the bone with a first pin disposed in said bone, comprising:

a convergence guide having a proximal side to be placed adjacent the entry surface of said bone, an opposite distal side, and a sidewall between said proximal and distal sides;

a cylindrical offset guide member containing along its length a plurality of parallel offset guide holes at predetermined distances from each other whereby any one of said guide holes can receive said second pin; and a cylindrical offset pivot member containing along its length a plurality of parallel offset pivot holes at predetermined distances from each other whereby the pivot member can slide over and pivot around said first pin through any one of said pivot holes;

said convergence guide defining a pair of cylindrical bores from said distal side to said proximal side formed to respectively slidably receive said offset guide member and said offset pivot member, said bores being spaced from each other a first predetermined distance on said distal side and a shorter predetermined distance on said proximal side so that any one of said offset guide holes converges with any one of said offset pivot holes at a point spaced at one of a plurality of predetermined distances from the proximal side of said convergence guide;

said convergence guide defining a pair of slots, each wider than the expected thickness of the pin thereat, formed entirely through said sidewall to and coextensive with respective bores whereby to enable release of said convergence guide from said pins by sliding said offset guide member and said offset pivot member out of their respective bores and then withdrawing said convergence guide while said pins pass through said slots and said pins remain in said bone.

10. The device of claim 9 in which each plurality of offset guide holes and offset pivot holes are disposed in a rectangular array of at least nine holes including a central hole, corner holes and side holes.

11. The device of claim 10 in which in each offset member the center-to-center distance between each side hole and said central hole is about 2 mm and the center-to-center distance between each corner hole and said central hole is about 3 mm.

12. The device of claim 9 in which said plurality of offset guide holes and offset pivot holes are disposed to converge at distances from the proximal side of said convergence guide in the range of about 30 mm to about 40 mm.

13. The device of claim 9 in which the proximal side of said convergence guide is concave.

14. An offset guide for drilling a second pin through a bone in parallel proximity to a first pin disposed in said bone, comprising a member having a plurality of parallel offset holes in the form of an array of at least 9 holes at predetermined distances from each other for enabling the guide to slide over and pivot around said first pin through one hole and receive said second pin through another hole and said array is rectangular array including a central hole, corner holes and side holes, the center-to-center distance between each said side hole and said central hole is about 2 mm and the center-to-center distance between each said corner hole and said central hole is about 3 mm 15. The device of claim 14 in which said member is cylindrical, said holes extending along its length said array is a rectangular array including a central hole, corner holes and side holes, the center-to-center distance between each side hole and side central hole is about 2 mm and the center-to-center distance between each corner hole and said central hole is about 3 mm" has been changed to read and said array is a rectangular array including a central hole, corner holes and side holes, the center-to-center distance between each side hole and said central hole is about 2 mm and the center-to-center distance between each corner hole and said central hole is about 3 mm.

16. An offset guide for drilling a second pin through a bone in parallel proximity to a first pin disposed in said bone, comprising a cylindrical member having a plurality of parallel offset holes along its length in the form of a rectangular array of at least 9 holes including a central hole, corner holes and side holes at predetermined distances from each other for enabling the guide to slide over and pivot around said first pin through one hole and receive said second pin through another hole, the center-to-center distance between each side hole and said central hole being about 2 mm and the center-to-center distance between each corner hole and said central hole being about 3 mm.

* * * * *